(12) United States Patent
Bottcher et al.

(10) Patent No.: US 9,585,384 B2
(45) Date of Patent: Mar. 7, 2017

(54) STABILIZATION OF COMPOUNDS COMPRISING IODINE

(71) Applicant: LANXESS Deutschland GmbH, Cologne (DE)

(72) Inventors: Andreas Bottcher, Cologne (DE); Bernd Koop, Cologne (DE); Peter Spetmann, Leverkusen (DE)

(73) Assignee: LANXESS Deutschland GmbH, Cologne (DE)

( * ) Notice: Subject to any disclaimer, the term of this patent is extended or adjusted under 35 U.S.C. 154(b) by 74 days.

(21) Appl. No.: 14/551,123

(22) Filed: Nov. 24, 2014

(65) Prior Publication Data

US 2015/0080491 A1 Mar. 19, 2015

Related U.S. Application Data

(62) Division of application No. 13/259,174, filed as application No. PCT/EP2010/053872 on Mar. 25, 2010, now Pat. No. 8,921,451.

(30) Foreign Application Priority Data

Apr. 1, 2009 (EP) .................................... 09157103

(51) Int. Cl.
| *A01N 43/44* | (2006.01) |
|---|---|
| *A01N 47/10* | (2006.01) |
| *C08L 67/06* | (2006.01) |
| *C08K 3/16* | (2006.01) |
| *C08K 5/3412* | (2006.01) |
| *C08K 5/205* | (2006.01) |
| *A01N 25/22* | (2006.01) |
| *C09D 5/14* | (2006.01) |

(52) U.S. Cl.
CPC ............. *A01N 25/22* (2013.01); *A01N 43/44* (2013.01); *C08K 5/205* (2013.01); *C08K 5/3412* (2013.01); *C08L 67/06* (2013.01); *C09D 5/14* (2013.01)

(58) Field of Classification Search
CPC ........ A01N 59/12; A01N 43/44; A01N 47/10; A01N 47/12; C08K 5/0058; C08K 5/205; C08K 5/3412; C08K 3/005; C08K 3/16
See application file for complete search history.

(56) References Cited

U.S. PATENT DOCUMENTS

| 3,547,688 A | * | 12/1970 | Gagliardi | ................ A61L 15/20 427/379 |
|---|---|---|---|---|
| 3,777,024 A | * | 12/1973 | Martin | ................... A01N 31/14 514/119 |
| 6,140,370 A | * | 10/2000 | Gaglani | .................. A01N 25/22 514/617 |
| 6,329,359 B1 | * | 12/2001 | Grammenos | .......... A01N 37/50 514/183 |
| 2004/0054067 A1 | * | 3/2004 | Rogmann | ................ C09G 1/10 524/556 |
| 2009/0036506 A1 | * | 2/2009 | Uhr | ...................... C07D 257/04 514/381 |

FOREIGN PATENT DOCUMENTS

DE CA 2175480 A1 * 5/1995 ............. A01N 25/22

* cited by examiner

*Primary Examiner* — Brieann R Fink

(57) ABSTRACT

Use of aziridines for stabilizing iodine-containing compounds, especially biocides.

16 Claims, No Drawings

STABILIZATION OF COMPOUNDS COMPRISING IODINE

This application is a divisional of pending U.S. patent application Ser. No. 13/259,174, filed 4 May 2012, with the same title, which claims the right of priority under 35 U.S.C. §119 (a)-(d) and 35 U.S.C. §365 of International Application No. PCT/EP10/53872, filed 25 Mar. 2010, which is entitled to the right of priority of European Patent Application No. EP 09157103.4 filed on 1 Apr. 2009.

The invention relates to the use of aziridine compounds for stabilizing iodine-containing compounds, especially biocides, to compositions of such combinations and to binder formulations comprising iodine-containing compounds, especially biocides, and aziridine compounds.

BACKGROUND AND PRIOR ART

Iodine-containing biocides are used for providing industrial materials, coating materials being an example, with protection from infestation, decomposition, destruction and visual alteration by fungi, bacteria and algae, preferentially by fungi. Furthermore, iodine-containing biocides, both alone and in combination with biocides from other classes of active ingredient, are used as components of biocidally active materials protection compositions such as wood preservatives. Besides iodoalkynyl compounds, the active ingredients used here include compounds in which one or more atoms of iodine are attached to double-bond systems, but also to singly bonded carbon atoms.

A behaviour common to many iodine-containing biocides is that on exposure to light even in bulk or as a component of an industrial material (coating material, for example) they lead to yellowing with breakdown of the active compound. This feature hinders or prevents the use of iodine-containing biocides in materials having such sensitivity, such as in light-coloured or white coating materials, for example.

Many iodine-containing biocides, particularly iodoalkynyl compounds, are destroyed with particular rapidity by metal compounds. This fact prevents iodoalkynyl compounds, for example, from being used in solvent-based coating materials, such as paints, varnishes and stains, for example, or in biocidal preservatives, such as wood preservative primers, wood preservative impregnation systems and wood preservative stains, for example, since these alkyd-based coating and preservation systems are regularly equipped with metal compounds. In such systems, transition metal compounds, examples being cobalt, lead, manganese and vanadium octoates, function as dryers (siccatives) for the alkyd resin-containing binder system. Moreover, transition metal compounds are also used as pigments, and in some cases have destructive properties comparable with the siccatives.

In the solvent-based systems referred to above, there are, in addition to the dryers, a series of further ingredients which, to different degrees, lead to breakdown of iodine-containing biocides. Whereas the destabilizing effect is still relatively weak with the solvents that are customarily used, the other customary components of a paint formulation, such as process additives, plasticizers, colour pigments, anti-settling agents, thixotropic agents, corrosion inhibitors, anti-skinning agents and binders, for example, exhibit more or less strongly pronounced destabilizing effects.

As well as in the solvent-based systems described above, problems also attend the use of iodine-containing biocides in certain water-based industrial materials (e.g. coating materials and preservatives such as wood preservative stains and primers). Where the film formation and film hardening of a water-based coating material is based, for example, on the oxidative crosslinking of water-soluble or emulsified alkyd resins, transition metal compounds are employed as siccatives in these systems as well, and their use is accompanied by destruction of the iodine-containing biocides present.

There are already methods known for preventing the degradation of halopropargyl compounds in transition-metal-containing, solvent-based alkyd-resin paints. WO 98/22543, for example, describes the addition of chelating reagents.

Iodine has been stabilized in JP-A-2006-45686, for example, by means of cyclodextrins (CD), the resulting complex being anchored more effectively on the fibre by polymerization of aziridine-containing monomers. In that case, however, the CD-iodine pairing is only a complex, with the iodine or iodophore lying protected in the cavity of the CD, without being bonded covalently to the CD. The iodophore itself, as well, is a complex, in which iodine is not covalently bonded to the support, particularly since this is only a form from which iodine must free itself again in order to achieve the desired effect.

Also known are transition-metal-containing, solvent-based alkyd-resin paints where halopropargyl compounds are stabilized by means of organic epoxides (cf. WO 00/16628). Epoxides for stabilizing IPBC have also already been described in JP-A-19-120515.

Moreover, there are already descriptions of methods of suppressing the light-induced degradation of active antifungal compounds, such as of iodopropargyl butylcarbamate, by addition of tetraalkylpiperidine compounds and/or UV absorbers (cf. EP-A 0083308).

According to WO 2007/028527, iodine-containing biocides are stabilized with 2-(2-hydroxyphenyl)benzotriazoles, and in WO 2005/027635 amphoteric compounds are used to stabilize IPBC.

Addition of epoxy compounds is said to reduce the discoloration of iodoalkyne compounds, such as IPBC (cf. U.S. Pat. No. 4,276,211 and U.S. Pat. No. 4,297,258).

Furthermore, there are descriptions of synergistic mixtures of epoxides with UV absorbers (cf. WO 99/29176) and with benzylidene camphor derivatives (cf. U.S. Pat. No. 6,472,424), which likewise exhibit reduced yellowing.

WO 2007/101549, moreover, describes the stabilization of iodine-containing biocides by means of azole compounds.

The stabilizing action of the aforementioned stabilizers, however, is not always sufficient, and carries performance disadvantages. Thus, in particular, the drying times of the paints are markedly prolonged, and in many cases this is unacceptable to the user. Moreover, the inhibition of discoloration is not always sufficient.

Surprisingly, it has now been found that, through the use of aziridine compounds, it is possible to provide iodine-containing compounds, especially biocides, particularly in solvent-based and water-based systems, with protection against both chemical and light-induced degradation, and hence to prevent the above-described disadvantages of unstabilized iodine-containing compounds, such as alterations to colour and loss of active compound/activity. It has been found, moreover, that using aziridine compounds to stabilize iodine-containing biocides in the aforementioned systems allows performance disadvantages to be avoided, such as the prolongation of the drying time of a coating system, for example.

Iodine-containing compounds in the context of this invention refer to organic compounds which possess at least one covalent iodine-carbon bond.

The invention therefore provides for the use of aziridine compounds for stabilizing iodine-containing compounds, more particularly biocides. Iodine-containing compounds contemplated are preferably iodoalkynyl compounds or compounds in which one or more iodine atoms are attached to double bonds or in which one or more iodine atoms are attached to singly bonded carbon atoms.

The iodine-containing compounds, more particularly biocides, are, for example, diiodomethyl p-tolyl sulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methylpropyl)-5-[(6-iodo-3-pyridinyl)methoxy]-3(2H)-pyridazinone (CAS RN: 120955-77-3), iodofenfos, 3-iodo-2-propynyl 2,4,5-trichlorophenyl ether, 3-iodo-2-propynyl 4-chlorophenyl formal (IPCF), N-iodopropargyloxycarbonylalanine, N-iodopropargyloxycarbonylalanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl)hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

The iodine-containing compounds, more particularly biocides, are preferably 3-iodo-2-propynyl 2,4,5-trichlorophenyl ether, 3-iodo-2-propynyl 4-chlorophenyl formal (IPCF), N-iodopropargyloxycarbonylalanine, N-iodopropargyloxycarbonylalanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl)hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

With particular preference the iodine-containing compounds, more particularly biocides, are iodopropynyl carbamates, more particularly 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl)hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

Furthermore, the particularly preferred iodine-containing compounds, more particularly biocides, are N-alkyl-iodotetrazoles, N-aryl-iodotetrazoles and N-aralkyl-iodotetrazoles.

The iodine-containing compounds, more particularly biocides, may be used individually or in mixtures together with two or more iodine-containing compounds, more particularly biocides. Particular preference is given to IPBC.

Aziridines contemplated are those which comprise one or more unsubstituted or substituted aziridine groups.

Preference is given, for example to aziridine compounds of the formula (I)

where
R$^1$ is hydrogen, alkyl or cycloalkyl, each of which are unsubstituted or substituted and/or mono- or polyethylenically unsaturated, or in each case substituted or unsubstituted fullerenyl, aryl, alkoxy, alkoxycarbonyl, arylcarbonyl or alkanoyl,
R$^2$, R$^3$, R$^4$ and R$^5$ independently of one another have the same definition as R$^1$ and additionally independently are halogen, hydroxyl, carboxyl, alkylsulphonyl, arylsulphonyl, nitrile, isonitrile, and
R$^2$ and R$^4$ or R$^3$ and R$^5$, together with the carbon atoms to which they are attached, form a 5- to 10-membered carbocyclic ring which is unsubstituted or substituted and/or mono- or polyethylenically unsaturated.

Monofunctional aziridines of the formula (I) that are contemplated are, for example, those in which R$^2$ and R$^4$ or R$^3$ and R$^5$, together with the carbon atoms to which they are attached, form a 5- to 10-membered carbocyclic ring which is unsubstituted or substituted and/or mono- or polyethylenically unsaturated.

These are, more particularly, those of the formula (II)

where the carbocyclic ring is unsubstituted or substituted by one or more substituents selected from the group consisting of halogen, hydroxyl, oxo, carboxyl, alkylsulphonyl, arylsulphonyl, nitrile, isonitrile, alkyl or cycloalkyl, each of which is unsubstituted or substituted and/or mono- or polyethylenically unsaturated, or substituted or unsubstituted fullerenyl, aryl, alkoxy, alkoxycarbonyl or alkanoyl, and
n is a number from 0 to 6, preferably from 0 to 1.

Likewise preferred are those monofunctional aziridine compounds of the formula (I) in which R$^1$ is a radical of the formula

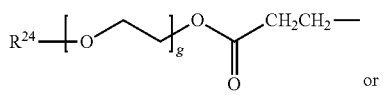

or

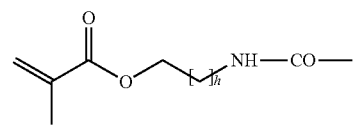

in which $R^{24}$ is —H or alkyl, preferably —H, —CH$_3$, —C$_2$H$_5$, more preferably —CH$_3$, —C$_2$H$_5$, g is a number from 1 to 4, preferably 1 to 3, more preferably 1 to 2, h is a number from 1 to 11, preferably 1 to 5 and more preferably 1 to 3, and the remaining radicals have the above definition.

More particular preference is given to those compounds of the formula (I) which conform to the compound of the formula (III) or (IV),

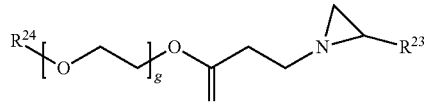
(III)

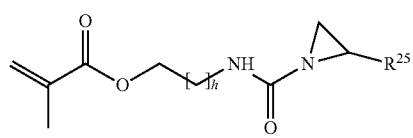
(IV)

where $R^{23}$ is —H or alkyl, preferably —H or —CH$_3$, more preferably —CH$_3$, $R^{25}$ is —H or alkyl, preferably —H or —CH$_3$, more preferably —CH$_3$, and the remaining radicals have the above definition.

Particularly preferred aziridines are those having two or more aziridine functions. Examples include compounds of the formula (V)

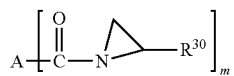
(V)

in which

A is an m-valent aliphatic, cycloaliphatic or aromatic radical, which is optionally substituted, m is a number from 2 to 5, more particularly 2 to 3, and $R^{30}$ for each m unit is in each case independently hydrogen or $C_1$-$C_4$ alkyl, more particularly CH$_3$ or CH$_2$CH$_3$.

Where m is 2, A is preferably $C_2$-$C_{10}$ alkylene.

more particularly

—((CH$_2$)$_6$)—, —C(CH$_3$)$_2$CH$_2$C(CH$_3$)$_2$CH$_2$— or

—C(CH$_3$)$_2$CH$_2$CH(CH$_3$)CH$_2$—, or is a phenylene, more particularly the bivalent radical of the formula

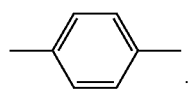

If m is 3, A is preferably the trivalent radical of the formula

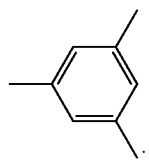

Preferred compounds of the formula (V) are those conforming to the formulae (Va)-(Vd).

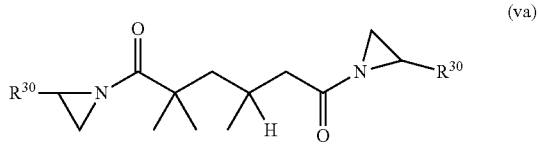
(va)

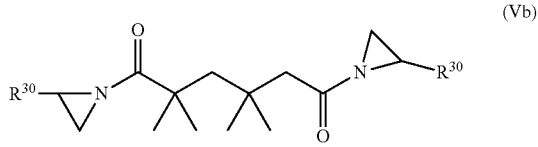
(Vb)

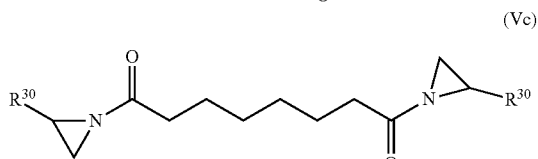
(Vc)

(Vd)

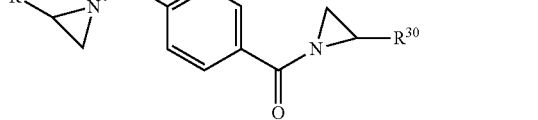

Likewise preferred as polyfunctional aziridine compounds are Michael adducts of optionally substituted ethylenimine with esters of polyhydric alcohols with α,β-unsaturated carboxylic acids and the adducts of optionally substituted ethylenimine with polyisocyanates.

Suitable alcohol components are, for example, trimethylolpropane, neopentylglycol, glycerol, pentaerythritol, 4,4'-isopropylidenediphenol and 4,4'-methylenediphenol. Examples of suitable α,β-unsaturated carboxylic acids include acrylic acid and methacrylic acid, crotonic acid and cinnamic acid.

With particular preference the composition of the invention comprises acrylic esters.

The corresponding polyhydric alcohols of the α,β-unsaturated carboxylic esters may optionally be alcohols which have been extended on their OH functions in some cases completely with alkylene oxides, singly or multiply. These may be, for example, the aforementioned alcohols extended singly or multiply with alkylene oxides. In this respect, reference is also made to U.S. Pat. No. 4,605,698, the disclosure content of which is included by reference in the present invention. Alkylene oxides which are particularly suitable in accordance with the invention are ethylene oxide and propylene oxide.

Examples of polyisocyanates suitable for reaction with optionally substituted ethylenimine are those specified at page 4 lines 33-35 of WO 2004/050617.

Examples of aziridines that are suitable in accordance with the invention are those specified at page 3 lines 29-34 of WO 2004/050617.

Preference is likewise given to those aziridines of the kind described, for example, in U.S. Pat. No. 3,225,013 (Fram), U.S. Pat. No. 4,490,505 (Pendergrass) and U.S. Pat. No. 5,534,391 (Wang).

Likewise preferred are those aziridines of the formula (I) which possess at least three aziridine groups, such as, for example, trimethylolpropane tris[3-(1-aziridinyl)propionate], trimethylolpropane tris[3-(2-methyl-1-aziridinyl)propionate], trimethylolpropane tris[2-aziridinylbutyrate], tris(1-aziridinyl)phosphine oxide, tris(2-methyl-1-aziridinyl)phosphine oxide, pentaerythritol tris-[3-(1-aziridinyl)propionate] and pentaerythritol tetrakis-[3-(1-aziridinyl)propionate].

Of these, preference is given particularly to trimethylolpropane tris[3-(1-aziridinyl)propionate], trimethylolpropane tris[3-(2-methyl-1-aziridinyl)propionate], trimethylolpropane tris[2-aziridinylbutyrate], pentaerythritol tris-[3-(1-aziridinyl)propionate] and pentaerythritol tetrakis-[3-(1-aziridinyl)propionate].

Particularly preferred are trimethylolpropane tris[3-(1-aziridinyl)propionate], trimethylolpropane tris[3-(2-methyl-1-aziridinyl)propionate] and pentaerythritol tetrakis-[3-(1-aziridinyl)propionate].

Likewise preferred are polyfunctional aziridines of the formula (VI)

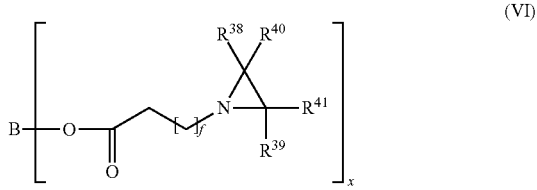

(VI)

in which
B is the radical of an aliphatic polyol which contains at least x OH functions, where x OH functions are substituted by the radical of the above brackets,
f is a number from 0 to 6, more particularly from 1 to 3,
x is a number greater than or equal to 2, and more particularly is 2 to 100 000, and
$R^{38}$ and $R^{39}$ or $R^{40}$ and $R^{41}$, together with the carbon atoms to which they are attached, form a 5- to 10-membered carbocyclic ring which is unsubstituted or substituted and/or mono- or polyethylenically unsaturated.

With particular preference B is the radical of a polyvinyl alcohol. Particularly preferred aziridines of the formula (VI) are those in which x is 3 or 4 and B is a trebly or quadruply OH-functional polyol.

Particularly preferred aziridines of the formula (VI) are those conforming to the formulae (VIa)-(VIc)

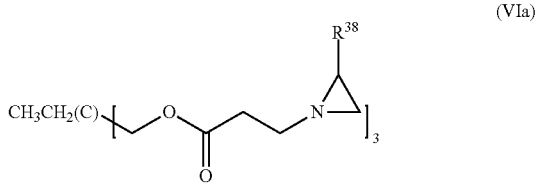

(VIa)

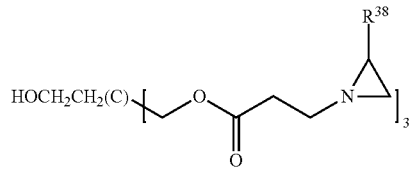

(VIb)

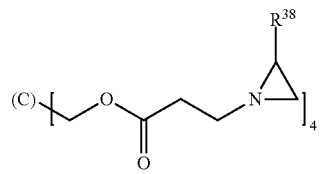

(VIc)

in which
$R^{38}$ is hydrogen or $CH_3$.

A particularly preferred product is the aziridine compound of the formula (VIa), with $R^{38}$=methyl, also known as Crosslinker CX-100 from DSM, and the hardener product "Corial Härter AN" from BASF, which comprises the aziridine of the formula (VIa) with $R^{38}$=hydrogen.

The aziridines for use in accordance with the invention are suitable preferentially for stabilizing iodine-containing compounds, more particularly biocides, in binder formulations, such as in alkyd-resin-based systems such as coating materials which comprise transition metal dryers. Preferred binder formulations and transition metal dryers are described in more detail later on below.

Stabilization in the context of this specification means preferably the stabilization of iodine-containing compounds against both chemical and light-induced degradation, particularly against chemical degradation.

The aziridine compounds may more particularly be used for suppressing or at least retarding the chemical degradation of iodine-containing compounds, more particularly biocides in active-compound formulations, more particularly coating materials such as paints, varnishes, primers, impregnating systems, stains and other industrial materials. The aziridine compounds that can be used in accordance with the invention for stabilizing iodine-containing compounds, more particularly biocides, have a good stabilizing action especially in alkyd-resin-based systems such as coating materials which comprise transition metal dryers.

The stabilization is preferably realised by the presence of the iodine-containing compounds, more particularly biocides, and the aziridine compound together in a mixture or in a medium.

The aziridine compound is employed preferably, in accordance with the invention, in a composition comprising
a) at least one iodine-containing biocide and
b) at least one aziridine compound.

The composition is likewise provided by the present invention.

With regard to the preferred iodine-containing compounds, more particularly biocides, and the preferred aziridine compounds, the forms of preference identified above apply to the preferred compositions of the invention as well.

Preferred Compositions Comprise
a) IPBC and
b) at least one aziridine of the formula (VI).

The compositions of the invention comprise in general 0.01%-70%, preferably 0.05%-60%, more preferably 0.1%-50% by weight of at least one iodine-containing compound, more particularly biocide, and 0.001%-50%, preferably 0.005%-40%, more preferably 0.01%-30% by weight of at least one aziridine compound.

The composition of the invention preferably comprises the iodine-containing compound, more particularly the iodine-containing biocide, and the aziridine compound in a sum total of 0.01% to 99% by weight.

In the context of the inventive use, it is usual to add 1% to 280% by weight of at least one aziridine compound, preferably 2% to 225% by weight, more particularly 5% to 110% by weight, based on the iodine-containing biocide.

Based on the iodine-containing compound it is preferred to use 0.05 to 5, preferably 0.1 to 4, more particularly 0.25 to 2 equivalents of the aziridine functions.

The composition of the invention may take a variety of forms, such as, for example, a solution, dispersion, solids mixture, etc., preferably a solution or dispersion.

Preferred compositions are those which comprise water and/or an organic solvent. Where water is utilised as an extender, it is also possible to use auxiliary solvents in the form of organic solvents which are suitable—that is, which can be mixed with water to form a phase.

Examples of organic solvents contemplated include aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, e.g. petroleum fractions (white spirit. Shellsol D60 from Shell Chemical), monohydric alcohols such as, for example, ethanol, isopropanol and butanol, polyhydric alcohols such as, for example, glycerol, pentaerythritol, polyvinyl alcohol (e.g. Mowiol® from Kuraray), glycols such as, for example, ethylene glycol and propylene glycol, oligoglycols and polyglycols, ethers of oligoglycols such as, for example, dipropylene glycol monomethyl ether (e.g. Dowanol® TPM from Dow), ethers and esters of alcohols such as (Texanol® from Eastman), ketones, such as acetone, methyl ethyl ketone, methyl isobutyl ketone or cyclohexanone, especially strongly polar aprotic solvents, such as dimethylformamide and dimethyl sulphoxide, and also, for example, totally etherified glycols, oligoglycols and polyglycols such as, for example, ethylene glycol dibutyl ether, etherified polyols and esterified polyols, esters of monobasic and polybasic carboxylic acids, e.g. diisobutyl adipate, diisobutyl maleate (e.g. Rhodiasolv DIB®).

However, the organic solvents referred to may also be employed preferably without or at least with a little water. Additionally to the components a) and b), the composition preferably comprises a solvent, more particularly a solvent composed to an extent of more than 95% by weight, preferably more than 98% by weight, of at least one organic solvent. Particularly preferred is a polar aprotic solvent, such as dimethylformamide and dimethyl sulphoxide, and also, for example, totally etherified glycols, oligoglycols and polyglycols, etherified polyols and esterified polyols, esters of monobasic and polybasic carboxylic acids, e.g. diisobutyl adipate, diisobutyl maleate (e.g. Rhodiasolv DIB®).

Further possible ingredients of the composition of the invention that may be used include adhesives such as carboxymethylcellulose, natural and synthetic polymers in powder, particle or latex form, such as gum arabic, polyvinyl alcohol, polyvinyl acetate, and also natural phospholipids, such as cephalins and lecithins, and synthetic phospholipids, and also mineral and vegetable oils. Moreover, it may comprise colorants such as inorganic pigments, e.g. iron oxide, titanium oxide, Prussian Blue, and organic dyes, such as alizarin dyes, azo dyes and metal phthalocyanine dyes, and trace nutrients, such as salts of iron, manganese, boron, copper, cobalt, molybdenum and zinc, and also stabilizers known for aziridine compounds, examples being tetramethylethylenediamine (TMEDA), triethylenediamine, and the 1,4-diazabicyclo[2.2.2]octane (DABCO) known from WO 2004/050617.

The invention further provides a process for preparing the composition of the invention.

The composition of the invention may be prepared, for example, by mixing the individual components, optionally with extenders, in other words liquid solvents, and with the optional use of further adjuvants.

The activity and the spectrum of action of the compositions of the invention and/or of the iodine-containing compound employed may be increased by adding, optionally, further antimicrobial compounds, fungicides, bactericides, herbicides, insecticides or other active compounds, so as to widen the spectrum of activity or to obtain particular effects, or by using such compounds at the same time. These mixtures may possess an even broader spectrum of action.

In many cases, synergistic effects are obtained, i.e. the activity of the mixture is greater than the activity of the individual components. The following compounds, for example, are particularly favorable co-components:

Triazoles Such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeconazole, (±)-cis-1-(4-chlorophenyl)-2-(1H-1,2,4-triazol-1-yl)cycloheptanol, 2-(1-ter-butyl)-1-(2-chlorophenyl)-3-(1,2,4-triazol-1-yl)propan-2-ol, tebuconazole, tetraconazole, triadimefon, triadimenol, triapenthenol, triflumizole, triticonazole, uniconazole and their metal salts and acid adducts;

Imidazoles Such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

Pyridines and Pyrimidines Such as:
ancymidol, buthiobate, fenarimol, mepanipyrin, nuarimol, pyvoxyfur, triamirol;

succinate dehydrogenase inhibitors such as:
benodanil, carboxim, carboxim sulphoxide, cyclafluramid, fenfuram, flutanil, furcarbanil, furmecyclox, mebenil, mepronil, methfuroxam, metsulfovax, nicobifen, pyracarbolid, oxycarboxin, Shirlan, Seedvax;

Naphthalene Derivatives Such as:
terbinafine, naftifine, butenafine, 3-chloro-7-(2-aza-2,7,7-trimethyloct-3-en-5-yne);

Sulphenamides Such as:
dichlofluanid, tolylfluanid, folpet, fluorofolpet, captan, captofol;

Benzimidazoles Such as:
carbendazim, benomyl, fuberidazole, thiabendazole or their sals;

Morpholine Derivatives Such as:
aldimorph, dimethomnorph, dodemorph, falimorph, fenpropidin, fenpropimorph, tridemorph, trimorphamid and their arylsulphonate salts such as, for example, p-toluenesulphonic acid and p-dodecylphenylsulphonic acid;

Benzothiazoles Such as:
2-meraptobenzothiazole;

Benzothiophene Dioxides Such as:
N-cyclohexyl-benzo[b]thiophenecarboxamide S,S-dioxide;

Benzamides Such as:
2,6-dichloro-N-(4-trifluoromethylbenzyl)benzamide, tecloftalam;

Boron Compounds Such as:
boric acid, boric esters, borax;

formaldehyde and formaldehyde-releasing compounds such as:
benzyl alcohol mono(poly)hemiformal, 1,3-bis(hydroxymethyl)-5,5-dimethylimidazolidine-2,4-dione (DMDMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis-(hydroxymethyl)urea, dazomet, dimethylolurea, 4,4-dimethyloxazolidine, ethylene glycol hemiformal, 7-ethylbicyclooxazolidine, hexahydro-S-triazine, hexamethylenetetramine, N-hydroxymethyl-N'-methylthiourea, methylenebismorpholine, sodium N-(hydroxymethyl)glycinate, N-methylolchloroacetamide, oxazolidine, parafownaldehyde, taurolin, tetrahydro-1,3-oxazine, N-(2-hydroxypropyl)aminemethanol, tetramethylolacetylenediuraea (TMAD);

Isothiazolinones Such as:
N-methylisothiazolin-3-one, S-chloro-N-methylisothiazolin-3-one, 4,5-dichloro-N-octylisothiazolin-3-one, 5-chloro-N-octylisothiazolinone, N-octylisothiazolin-3-one, 4,5-trimethylenisothiazolinone, 4,5-benzoisothiazolinone;

Aldehydes Such as:
cinnamaldehyde, formaldehyde, glutaraldehyde. β-bromocinnamaldehyde, o-phthalaldehyde;

Thiocyanates Such as:
thiocyanatomethylthiobenzothiazole, methylenebisthiocyanate;

Quaternary Ammonium Compounds and Guanidines Such as:
benzalkonium chloride, benzyldimethyltetradecylammonium chloride, benzyldimethyl-dodecylammonium chloride, dichlorobenzyldimethylalkylammonium chloride, didecyldimethyl-ammonium chloride, dioctyldimethylammonium chloride, N-hexadecyltrimethylammonium chloride, 1-hexadecylpyridinium chloride, iminoctadine tris(albesilate);

Phenols Such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;

Microbicides with an Activated Halogen Group Such as:
bronopol, bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloracetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl 2-chlorocyanovinyl sulphone, phenyl 1,2-dichloro-2-cyanovinyl sulphone, trichloroisocyanuric acid;

Pyridines Such as:
1-hydroxy-2-pyridinethione (and the Cu, Na, Fe, Mn, Zn salts thereof), tetrachloro-4-methyl-sulphonylpyridine, pyrimethanol, mepanipyrim, dipyrithion, 1-hydroxy-4-methyl-6-(2,4,4-trimethylpentyl)-2(1H)-pyridine;

Methoxyacrylates or Similar Such as:
azoxystrobin, dimoxystrobin, fluoxastrobin, kresoximmethyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS No. 185336-79-2);

Metal Soaps Such as:
salts of the metals tin, copper and zinc with higher fatty acids, resin acids, naphthenic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

Metal Salts Such as:
salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;

Oxides Such as:
oxides of the metals tin, copper and zinc, such as, for example, tributyltin oxide, $Cu_2O$, CuO, ZnO;

Oxidizing Agents Such as:
hydrogen peroxide, peracetic acid, potassium persulphate;

Dithiocarbamates Such as:
cufraneb, ferban, potassium N-hydroxymethyl-N'-methyldithiocarbamate, sodium dimethyldithiocarbamate, potassium dimethyldithiocarbamate, mancozeb, maneb, metam, metiram, thiram, zineb, ziram;

Nitriles Such as:
2,4,5,6-tetrachloroisophthalonitrile, disodium cyanodithioimidocarbamate;

Quinoines Such as:
8-hydroxyquinoline and the copper salts thereof;

Other Fungicides and Bactericides Such as:
bethoxazin, 5-hydroxy-2(5H)-furanone, 4,5-benzodithiuzolinone, 4,5-trimethylenedithiazolinone, N-(2-p-chlorobenzoylethyl)hexaminium chloride, 2-oxo-2-(4-hydroxyphenyl)acetohydroxy-cinnamoyl chloride, tris-N-(cyclohexyldiazeniumdioxy)-aluminium, N-(cyclohexyldiazenium-dioxy)-tributyltin or its potassium salts, bis-N-(cyclohexyldiazeniumdioxy) copper, iprovalicarb, fenhexamide, spiroxamine, carpropamid, diflumetorin, quinoxyfen, faimoxadone, polyoxorim, acibenzolar S-methyl, furametpyr, thifluzamide, methalaxyl-M, benthiavalicarb, metrafenon, cyflufenamid, tiadinil, tea tree oil, phenoxyethanol,
Ag, Zn or Cu-containing zeolites alone or incorporated into polymeric materials.

Very Especially Preferred are Mixtures with
azaconazole, bromuconazole, cyproconazole, dichlobutrazol, diniconazole, diuron, hexaconazole, metaconazole, penconazoJe, propiconsazole, tebuconazole, dichlofluanid, tolyifluanid, fluorfolpet, methfuroxam, carboxin, N-cyclohexyl-benzo[b]thiophenecarboxamide S,S-dioxide, fenpiclonil, 4-(2,2-difluoro-1,3-benzodioxol-4-yl)-

1H-pyrrole-3-carbonitrile, butenafine, imazalil, N-methylisothiazolin-3-one, 5-chloro-N-methylisothiazolin-3-one, N-octylisothiazolin-3-one, dichloro-N-octylisothiazolinone, mercaptobenzothiazole, thiocyanatomethylthiobenzothiazole, thiabendazole, benzoisothiazolinone, N-(2-hydroxypropyl)aminomethanol, benzyl alcohol (hemi)formal, N-methylolchloroacetamide, N-(2-hydroxypropyl)aminemethanol, glutaraldehyde, omadline, Zn-omadine, dimethyl dicarbonate, 2-bromno-2-nitro-1,3-propunediol, bethoxazin, o-phthalialdehyde, 2,2-dibromo-3-nitrilepropionamide, 1,2-dibromo-2,4-dicyanobutane, 1,3-bis(hydroxymethyl)-5,5-dimethylimidazolidine-2,4-dione (DMDMH), tetra-methylolacetylenediurea (TMAD), ethylene glycol hemiformal, p-hydroxybenzoic acid, carbendazim, chlorophen, 3-methyl-4-chlorophenol, o-phenylphenol.

Apart from with the abovementioned fungicides and bactericides, mixtures with a good efficacy are, moreover, also prepared with other active compounds:

insecticides/acaricides/nematicides:

abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtn, azinpbos A, azinphos M, azocyclotin,

*Bacillus thuringiensis*, barthrin, 4-bromo-2-(4-chlorophenyl)-1-(ethoxymethyl)-5-(trifluoromethyl)-1H-pyrrole-3-carbonitrile, bendiocarb, benfuracarb, bensuhanp, betacyfluthrin, bifenthrin, bioresmethrin, bioallethrin, bistrilfluoron, bromophos A, bromnophos M, bufencarb, buprofezin, butathiophos, butocarboxim, butoxycarboxim, cadusafos, carbaryl, carbofuran, carbophenothion, carbosulfan, cartap, quinomethionate, cloethocarb, chlordane, chlorethoxyfos, chlorfenapyr, chlorfenvinphos, chlorfluazuron, chlormephos, N-[(6-chloro-3-pyridinyl)methyl]-N'-cyano-N-methylethaneimidamide, chlorpicrin, chlorpyrifos A, chlorpyrifos M, cis-resmnethrin, clocythrin, clothiazoben, cypophenothrin, clofentezin, coumaphos, cyanophos, cycloprothrin, cyfludhin, cyhalothin, cyhexatin, cypermethrin, cyromain.

decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl(4-ethoxyphenyl)silylmethyl-3-phenoxybenzyl ether, dimethylvinphos, dioxathion, disulfoton, eflusilanate, emamectin, empenthrin, endosulfan, EPN, esfenvulerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion, fenvalerate, fipronil, flonicamnid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmetilan, fosthiazate, fubfenprox, furathiocarb, halofenozide, HCH, (CAS RN: 58-89-9), heptenophos, hexaflumuron, hexythiazox, hydramethylnon, hydroprene, imidacloprid, imiprothrin, indoxycarb, iprinomectin, iprobenfos, isazophos, isoamidophos, isofenphos, isoprocarb, isoprothiolane, isoxathion, ivernmectin, kadedrin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxiectin, naled, NI 125, nicotine, nitenpyram, noviflumuron, omethoate, oxamyl, oxydemethon M, oxydeprofos, parathion A, parathion M, penfluoron, permethrin, 2-(4-phenoxyphenoxy)ethyl ethylcarbamate, phenthoate, phorate, phosalon, phosmet, phosphamidon, phoxim, pirimicarb, pirimiphos M, pirimiphos A, prallethrn, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium, quinalphos, resmethrin, rotenone, salithion, sebufos, silafluofen, spinosad, spirodiclofen, spiromesifen, sulfotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamnate, tinazuron, trichlorfon, triflumnuron, trimethacarb, vamidothion, xylylcarb, zetamethrin;

Molluscicides:

fentin acetate, metaldehyde, methiocarb, niclosamide;

Herbicides and Algicides:

acetochlor, acifluorfen, aclonifen, acrolein, alachlor, alloxydim, ametryn, amidosulfuron, amitrole, ammonium sulfamate, anilofos, asulam, atrazine, azafenidin, aziphbotryne, azimsulfuron, benazolin, benfluralin, benfuresate, bensulfuron, bensulfide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinosulfuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyctosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn.

eglinazine, endothal, EPTC, esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, fluorochloridone, fluoroxypyr, fomesafen, fosamine, fosametine, flamprop-isopropyl, flamprop-isopropyl-L, flufenpyr, flumicloracpentyl, flumipropyn, flumioxzim, flurtamone, flumioxzim, flupyrsulfuron-methyl, fluthiacet-methyl,
glyphosate, glufosinate-ammonium
haloxyfop, hexazinone,
imazamethabenz, isoproturon, isoxaben, isoxapyrifop, imazapyr, imazaquin, imazethapyr, ioxynil, isopropalin, imazozsulfuron, imazomiox, isoxaflutole, imazapic.
ketospiradox,
lactofen, lenacil, linuron,
MCPA, MCPA-hydrazide, MCPA-thioethyl, MCPB, mecoprop, mecoprop-P, mefenacet, mefluidide, mesosulfuron, metam, metamifop, metamitron, metazachlor, methabenzthiazuron, methazole, methoroptryne, methyldymron, methyl isothiocyanate, metobromuron, metoxuron, metribuzin, metsulfuron, molinate, manolide, monolinuron, MSMA, metolachlor, metosulam, metobenzuron,
naproanilide, napropamide, naptalam, neburon, nicosulfuron, norflurazon, sodium chlorate,
oxadiazon, oxyfluorfen, oxysulfuron, orbencarb, oryzalin, oxadiargyl,
propyzamide, prosulfocarb, pyrazolate, pyrazosulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloramn, piperophos, pretilachlor, primisulfuron, prodiamine, profoxydim, prometryn, propachlor, propanil, propaquizafob, propazine, propham, propisochlor, pyriminobac-methyl, pelargonic acid, pyrithiobac, pyraflufen-ethyl,
quinmerac, quinocloamine, quizalofop, quizalofop-P, quinchlorac,
rimsulfuron,
sethoxydim, sifuron, simazine, simetryn, sulfosulfuron, sulfometuron, sulfentrazone, sulcotrione, sulfosate,
tar oils, TCA, TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluoralin, tycor, thdiazimin, thiazopyr, triflusulfuron,
vernolate.

The invention further provides a binder formulation comprising
at least one binder,
at least one iodine-containing compound, more particularly biocide, and
at least one aziridine compound.

Preferably the binder formulation comprises the iodine-containing compound, more particularly biocide, component and the aziridine compound component in the form of the composition of the invention. Preferred binders contemplated include oxidatively drying binders, preferably alkyd-resin-based binders, or binders which form films by means of coalescents, especially latices. The alkyd-resin-based binders contemplated are preferably alkyd resins, inclusive of their modified alkyd resins.

The alkyd resins are, in general, polycondensation resins formed from polyols and polybasic carboxylic acids and/or their anhydrides, and fats, oils or free natural and/or synthetic fatty acids. The alkyd resins may optionally also be modified chemically with hydrophilic groups, especially water-soluble groups, in order that they can be used, for example, as an emulsifiable or as a water-soluble alkyd resin.

The stated polyols are preferably glycerol, pentaerythritol, trimethylolethane, trimethylolpropane and various diols such as ethane-/propanediol, diethylene glycol and neopentyl glycol.

The stated polybasic carboxylic acids and/or their anhydrides are preferably phthalic acid, phthalic anhydride, maleic anhydride, isophthalic acid, terephthalic acid, trimellitic anhydride, adipic acid, azelaic acid or sebacic acid.

The stated oils or fatty acids are generally linseed oil, oiticica oil, tung oil, soya oil, sunflower oil, safflower oil, ricinene oil, tall oil, castor oil, coconut oil, peanut oil, their fatty acids, and also synthetic monocarboxylic acids.

The alkyd resins can optionally also be modified with, for example, natural resins, phenolic resins, acrylic resins, styrene, epoxy resins, silicone resins, isocyanates, polyamides or aluminium alkoxides.

The alkyd resins generally have a molar mass of 500 to 100 000 g/mol, preferably of 1000 to 50 000 g/mol, more particularly of 1500 to 20 000 g/mol, determined preferably by laser light scattering, see, for example, "Static Light Scattering of Polystyrene Reference Materials: Round Robin Test". U. Just, B. Werthmann International Journal of Polymer Analysis and Characterization, 1999 Vol. 5, pages 195-207.

The binder formulations of the invention comprise preferably 1% to 80%, more preferably 2% to 70% and with particular preference 3% to 60% by weight of alkyd resin.

The binder formulation of the invention preferably comprises an alkyd-resin-based binder and a transition metal dryer for oxidative drying. Transition metal dryers for the purposes of this specification are more particularly transition metal compounds which accelerate the drying and curing of the alkyd-resin-based binder.

Preference is given to the salts of transition metals of groups Vb, VIb, VIIb, VIII and Ib of the chemical periodic system. These are more particularly the salts of cobalt, manganese, vanadium, nickel, copper and iron, more preferably cobalt, manganese, iron and vanadium. They need not necessarily be used alone, but instead can also be employed in combination with non-transition metal salts, such as lead, calcium or zirconium, for example.

The preferred transition metal salts are soluble in white spirit at 20° C. in an amount of more than 10 g/l. The salts in question are preferably the salts of carboxylic acids, which have high compatibility with the alkyd resin binders and at the same time ensure sufficient solubility of the metal salt. Preference is given to using transition metal salts of fatty acids, such as oleates or linoleates, resin acids such as resinates, or salts of 2-ethylhexanoic acid (octoates). Preferred transition metal dryers are cobalt octoate and cobalt naphthenate, e.g. Octasoligen®-Cobalt 12 from Borchers.

The binder formulations of the invention preferably comprise the transition metal dryers in an amount of 0.001% to 1%, preferably 0.005% to 0.5% and very preferably 0.01% to 0.1% by weight, based in each case on binder.

In one preferred embodiment the binder formulations comprise at least one polar organic solvent, preferably a polar protic solvent. Examples of suitable such polar protic solvents are those such as dipropylene glycol monomethyl ether (e.g. Dowanol DPM from Dow Chemical) and also, preferably, in combination thereto, polar aprotic solvents, such as dimethylformamide and dimethyl sulphoxide, and also, for example, etherified glycols, oligoglycols and polyglycols, etherified polyols and esterified polyols, esters of monobasic and polybasic carboxylic acids, e.g. diisobutyl adipate, diisobutyl maleate, (e.g. Rhodiasolv DIB).

Particular preference is given to the binder formulation comprising
1% to 80%, preferably 2% to 70%, more preferably 3% to 60% by weight of alkyd resin binder(s)

0% to 50%, preferably 0% to 45%, more preferably 0% to 40% by weight of colour pigments 0.01% to 5%, preferably 0.05% to 3%, more preferably 0.1% to 2% by weight of iodine-containing compound, more particularly biocide 0.001% to 5%, preferably 0.005% to 3%, more preferably 0.01% to 2% by weight of aziridine compound 2% to 97% by weight of solvent(s), more particularly polar solvents, including up to 10%, more particularly 0.01% to 7.5%, by weight, based on the binder preparation, of polar aprotic solvents, and 0.001% to 3% by weight of a transition metal dryer.

Particularly preferred binder formulations of the invention are those comprising at least one alkyd resin, at least one transition metal dryer, IPBC, at least one aziridine compound and at least one solvent.

The binder formulation may further comprise fillers, anti-skinning agents, rheological additives such as, for example, anti-settling agents and thixotropic agents, further biocides such as fungicides, bactericides, anti-fouling agents and algicides, solvents, process additives, plasticizers, UV stabilizers and heat stabilizers, and also corrosion inhibitors, in customary amounts.

It is additionally possible to add further stabilizers to the binder formulations, examples being the chelating reagents specified in WO 98/22543, or the organic epoxides specified in WO 00/16628. In many cases synergistic effects are observed here.

In the context of the inventive use it is also possible, furthermore, to add one or more stabilizers from the group consisting of antioxidants, free-radical scavengers, UV stabilizers, chelators and UV absorbers, which in some cases exhibit synergistic effects.

Further UV stabilizers that may be mentioned include, by way of example, the following: sterically hindered phenols, such as 2,6-di-tert-butyl-4-methylphenol, 2-tert-butyl-4,6-dimethylphenol, 2,6-di-cyclopentyl-4-methylphenol, 2-(α-methylcyclohexyl)-4,6-dimethylphenol, 2,6-di-octadecyl-4-methylphenol or 2,6-di-tert-butyl-4-methoxymethylphenol, diethyl(3,5-di-tert-butyl-4-hydroxybenzyl)phosphonate, 2,4-dimethyl-6-(1-methylpentadecyl)phenol, 2-methyl-4,6-bis[(octylthio)methyl]phenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis(4-methyl-6-cyclohexylphenol), 2,2'-methylenebis(4,6-di-tert-butylphenol), 2,2'-ethylidenebis(4,6-di-tert-butylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 1,1,3-tris(5-tert-butyl-4-hydroxy-2-methylphenyl)butane, 1,3,5-tri(3,5-di-tert-butyl-4-hydroxybenzyl)-2,4,6-trimethylbenzene, isooctyl 3,5-di-tert-butyl-4-hydroxybenzylmercaptoacetate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 1,3,5-tris[(3,5-di-tert-butyl-4-hydroxyphenyl)propionyloxyethyl]isocyanurate, dioctadecyl 3,5-di-tert-butyl-4-hydroxybenzylphosphonate, calcium monoethyl 3,5-di-tert-butyl-4-hydroxybenzylphosphonate, N,N'-di-(3,5-di-tert-butyl-4-hydroxyphenylpropionyl)hexamethylenediamine, N,N'-di-(3,5-di-tert-butyl-4-hydroxyphenylpropionyl)trimediylenediamine, N,N'-di-(3,5-di-tert-butyl-4-hydroxyphenylpropionyl)hydrazine, 3,9-bis[1,1-dimethyl-2-[(3-tert-butyl-4-hydroxy-5-methyl phenyl)propionyloxy]ethyl]-2,4,8,10-tetraoxaspiro[5,5]undecane, bis[3,3-bis(4'-hydroxy-3'-tert-butylphenyl)butanoic acid]ethylene glycol ester, 2,6-bis[[3-(1,1-dimethylethyl)-2-hydroxy-5-methylphenyl]octahydro-4,7-methano-1H-indenyl]-4-methylphenol (=Wingstay L), 2,4-bis(n-octylthio)-6-(3,5-di-tert-butyl-4-hydroxyphenylamino)-s-triazine, N-(4-hydroxyphenyl)octadecaneamide, 2,4-di-tert-butylphenyl 3',5'-di-tert-butyl-4'-hydroxybenzoate, (benzoic acid, 3,5-bis(1,1-dimethylethyl)-4-hydroxy-, hexadecyl ester), 3-hydroxyphenyl benzoate, 2,2'-methylenebis(6-tert-butyl-4-methylphenol)monoacrylate, 2-(1-dimethylethyl)-6-[1-[3-(1,1'-dimethylethyl)-5-(1,1-dimethylpropyl)-2-hydroxyphenyl]ethyl]-4-(1-dimethylpropyl)phenyl ester, esters of β-(3,5-di-tert-butyl-4-hydroxyphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide, esters of β-(5-tert-butyl-4-hydroxy-3-methylphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Hindered Amines, Such as bis(1,2,2,6,6-pentamethyl-4-piperidyl)2-(3,5-di-tert-butyl-4-hydroxybenzyl)-2-butylmalonate, bis(2,2,6,6-tetramethyl-4-piperidyl)decanedioate, dimethyl succinate-1-(2-hydroxyethyl)-4-hydroxy-2,2,6,6-tetramethylpiperidine copolymer, poly[[6-[(1,1,3,3-tetramethylbutyl)amino]-1,3,5-triazine-2,4-diyl][(2,2,6,6-tetramethyl-4-piperidyl)imino]hexamethylene[(2,2,6,6-tetramethyl-4-piperidyl)imino]] (CAS No. 71878-19-8), 1,5,8,12-tetrakis[4,6-bis(n-butyl-n-1,2,2,6,6-pentamethyl-4-piperidylamino)-1,3,5-triazin-2-yl]-1,5,8,12-tetrazadodecane (CAS No. 106990-43-6), bis(1,2,2,6,6-pentamethyl-4-piperidyl)decanedioate, bis(1,2,2,6,6-pentamethyl-4-piperidyl)2-(3,5-di-tert-butyl-4-hydroxybenzyl)-2-butylmalonate, decanedioic acid, bis(2,2,6,6-tetramethyl-4-piperidinyl)ester, reaction products with tert-butyl hydroperoxide and octane (CAS No. 129757-67-1), Chimasorb, 2020 (CAS No. 192268-64-7), poly[(6-morpholino-1,3,5-triazine-2,4-diyl][(2,2,6,6-tetramethyl-4-piperidiny)imino]-1,6-hexanediyl[(2,2,6,6-tetramethyl-4-piperidinyl)imino]], poly[[6-(4-morpholinyl)-1,3,5-triazine-2,4-diyl][(1,2,2,6,6-pentamethyl-4-piperidinyl)imino]-1,6-hexanediyl[(1,2,2,6,6-pentamethyl-4-piperidinyl)imino]] (9CI), 3-dodecyl-1-(2,2,6,6-tetramethyl-4-piperidyl)pyrrolidine-2,5-dione, 3-dodecyl-1-(1,2,2,6,6-pentamethylpiperidin-1-yl)pyrrolidine-2,5-dione, 4-octadecanoyloxy-2,2,6,6-tetramethylpiperidine, poly[[6-(cyclohexylamino)-1,3,5-triazine-2,4-diyl][(2,2,6,6-tetramethyl-4-piperidinyl)imino]-1,6-hexanediyl[(2,2,6,6-tetramethyl-4-piperidinyl)imino]], 1H,4H,5H,8H-2,3a,4a,6,7a8a-hexaazacyclopenta[def]fluorene-4,8-dione, hexahydro-2,6-bis(2,2,6,6-tetramethyl-4-piperidinyl)-(CAS No. 109423-00-9), N,N'-bis(formyl)-N,N'-bis(2,2,6,6-tetramethyl-4-piperidyl)-1,6-hexanediamine, N-(tetramethyl-4-piperidinyl)maleimide-C20-24-α-olefin copolymer (CAS No. 199237-39-3), tetrakis(1,2,2,6,6-pentamethyl-4-piperidyl) 1,2,3,4-butanetetracarboxylate, tetrakis(2,2,6,6-tetramethyl-4-piperidyl) 1,2,3,4-butanetetracarboxylate, 1,2,2,6,6-pentamethyl-4-piperidinyl tridecyl 1,2,3,4-butanetetracarboxylate, (1,2,3,4-butanetetracarboxylic acid, 2,2,6,6-tetramethyl-4-piperidinyl tridecyl ester), (2,4,8,10-tetraoxaspiro[5.5]undecane-3,9-diethanol, β,β,β',β'-tetramethyl-, polymer with 1,2,3,4-butanetetrahcarboxylic acid) (CAS No. 115055-30-6), 2,2,4,4-tetramethyl-21-oxo-7-oxa-3,20-diazadispiro[5.1.11.2]heneicosane, (7-oxa-3,20-diazaispiro[5.1.11.2]heneicosane-20-propanoic acid, 2,2,4,4-tetramethyl-21-oxo-, tetradecyl ester), (7-oxa-3,20-diazadiaspiro[5.1.11.2]heneicosan-21-one, 2,2,4,4-tetramethyl-20-(oxiranylmethyl)-), (propanamide, N-(2,2,6,6-tetramethyl-4-piperidinyl)-3-[(2,2,6,6-tetramethyl-4-piperidinyl)amino]-), (1,3-propanediamine, N,N'''-1,2-ethanediylbis-, polymer with 2,4,6-trichloro-1,3,5-triazine, reaction products with N-butyl-2,2,6,6-tetramethyl-4-piperidinamine) (CAS No. 136504-96-6), 1,1'-ethylenebis(3,3,5,5-tetramethyl-2-piperazinone), (piperazinone, 1,1',1''-[1,3,5-triazine-2,4,6-triyltris-[(cyclohexylimino)-2,1-ethanediyl]]tris-3,3,5,5-tetramethyl-), (7-oxa-3,20-diazadispiro[5.1.11.2]-heneicosane-20-propanoic acid, 2,2,4,4-tetramethyl-21-oxo-, dodecyl ester), 1,1-bis(1,2,2,6,6-pentamethyl-4-piperidyloxycarbonyl)-2-(4-methoxyphenyl) ethene, (2-propenoic acid, 2-methyl-, methyl ester, polymer with 2,2,6,6-tetramethyl-4-piperidinyl 2-propenoate) (CAS No. 154636-12-1), (propanamide, 2-methyl-N-(2,2,6,6-tetramethyl-4-piperidinyl)-2-[(2,2,6,6-tetramethyl-4-piperidinyl)amino]-), (D-glucitol, 1,3:2,4-bis-O-(2,2,6,6-tetramethyl-4-piperidinylidene)-) (CAS No. 99473-08-2), N,N'-bis(2,2,6,6-tetramethyl-4-piperidinyl)isophthalamide, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, 1-(4-tert-butyl-2-butenyl)-4-hydroxy-2,2,6,6-tetramethylpiperidine, 4-stearoyloxy-2,2,6,6-tetramethylpiperidine, 1-ethyl-4-salicyloyloxy-2,2,6,6-tetramethylpiperidine, 4-methacryloyl-oxy-1,2,2,6,6-pentamethylpiperidine, 1,2,2,6,6-pentamethylpiperidin-4-yl β-(3,5-ditert-butyl-4-hydroxyphenyl)propionate, 1-benzyl-2,2,6,6-tetramethyl-4-piperidinyl maleate, (di-2,2,6,6-tetramethylpiperidin-4-yl)adipate, (di-2,2,6,6-tetramethylpiperidin-4-yl)sebacate, (di-1,2,3,3,6-tetramethyl-2,6-diethylpiperidin-4-yl)sebacate, (di-1-allyl-2,2,6,6-tetramethylpiperidin-4-yl)phthalate, 1-propargyl-4-β-cyanoethyl-oxy-2,2,6,6-tetramethylpiperidine, 1-acetyl-2,2,6,6-tetramethylpiperidin-4-yl acetate, trimellitic acid tri-2,2,6,6-tetramethylpiperidin-4-yl)ester, 1-acryloyl-4-benzyloxy-2,2,6,6-tetramethylpiperidine, dibutyl-malonic acid di(1,2,2,6,6-pentamethylpiperidin-4-yl)ester, butyl(3,5-di-tert-butyl-4-hydroxybenzyl)malonic acid di(1,2,2,6,6-pentamethylpiperidin-4-yl)ester, dibenzylmalonic acid di(1,2,2,6,6-pentamethylpiperidin-4-yl)ester, dibenzylmalonic acid di(1,2,3,6-tetramethyl-2,6-diethylpiperidin-4-yl)ester, hexane-1',6'-bis-(4-carbamoyloxy-1-n-butyl-2,6,6-tetramethylpiperidine), toluene-2',4'-bis(4-carbamoyloxy-1-n-propyl-2,2,6,6-tetramethylpiperidine), dimethyl-bis(2,2,6,6-tetramethylpiperidine-4-oxy)silane, phenyl-tris(2,2,6,6-tetramethylpiperidine-4-oxy)silane, tris(1-propyl-2,2,6,6-tetramethylpiperidin-4-yl)phosphite, tris(1-propyl-2,2,6,6-tetramethylpiperidin-4-yl)phosphate, phenyl[bis(1,2,2,6,6-pentamethylpiperidin-4-yl)phosphonate, di(1,2,2,6,6-pentamethylpiperidin-4-yl)sebacate, N,N'-bis(2,2,6,6-tetramethylpiperidin-4-yl)hexamethylene-1,6-diamine, N,N'-bis(2,2,6,6-tetramethylpiperidin-4-yl)hexamethylene-1,6-diacetamide, 1-acetyl-(N-cyclohexylacetamido)-2,2,6,6-tetramethylpiperidine, 4-benzylamino-2,2,6,6-tetramethylpiperidine, N,N'-bis(2,2,6,5-tetramethylpiperidin-4-yl)-N,N'-dibutyladipamide, N,N'-bis(2,2,6,6-tetramethylpiperidin-4-yl)-N,N'-dicyclohexyl(2-hydroxypropylene), N,N'-bis(2,2,6,6-tetramethylpiperidin-4-yl)-p-xylylenediamine, 4-(bis-2-hydroxyethyl)amino-1,2,2,6,6-pentamethylpiperidine, 4-(3-methyl-4-hydroxy-5-tert-butyl-benz-amido)-2,2,6,6-tetramethylpiperidine, 4-methacrylamino-1,2,2,6,6-pentamethylpiperidine, 9-aza-8,8,10,10-tetramethyl-1,5-dioxaspiro[5.5]undecane, 9-aza-8,8,10,10-tetramethyl-3-ethyl-1,5-dioxaspiro[5.5]undecane, 8-aza-2,7,7,8,9,9-hexamethyl-1,4-dioxaspiro[4.5]decane, 9-aza-3-hydroxymethyl-3-ethyl-8,8,9,10,10-pentamethyl-1-5-dioxaspiro[5.5]undecane, 9-aza-3-ethyl-3-acetoxymethyl-9-acetyl-8,8,10,10-tetramethyl-1,5-dioxaspiro[5.5]undecane, 2,2,6,6-tetramethylpiperidine-4-spiro-2'-(1,3'-dioxane)-5'-spiro-5''-(1''',3'''-dioxane)-2''-spiro-4''-(2''',2''',6''',6'''-tetramethylpiperidine)-3-benzyl-1,3,8-triaza-7,7,9,9-tetra-methyl-spiro[4.5]decane-2,4-dione, 3-n-octyl-1,3,8-triaza-7,7,9,9-tetramethyl-spiro-[4.5]decane-2,4-dione, 3-allyl-1,3,8-triaza-1,7,7,9,9-pentamethyl-spiro[4.5]decane-2,4-dione, 3-glycidyl-1,3,8-triaza-7,7,8,9,9-pentamethyl-spiro[4.5]decane-2,4-dione, 2-isopropyl-7,7,9,9-tetramethyl-1-oxa-3,8-diaza-4-oxyspiro[4.5]decane, 2-butyl-7,7,9,9-tetramethyl-1-oxa-3,8-diaza-4-oxyspiro[4.5]decane, 2-isopropyl-7,7,9,9-tetramethyl-1-oxa-4,8-diaza-oxyspiro[4.5]decane, 2-butyl-7,7,9,9-tetramethyl-1-oxa-4,8-diaza-3-oxyspiro[4.5]decane, bis[β-(2,2,6,6-tetramethylpiperidino)ethyl]sebacate, α-(2,2,6,6-tetramethylpiperidino)acetic acid n-octyl ester, 1,4-bis(2,2,6,6-tetramethylpiperidino)-2-butene, N-hydroxymethyl-N'-2,2,6,6-tetramethylpiperidin-4-ylurea, N-methoxymethyl-N'-2,2,6,6-tetramethylpiperidin-4-ylurea, N-methoxymethyl-N'-n-dodecyl-N'-2,2,6,6-tetramethylpiperidino-4-ylurea, O-(2,2,6,6-tetramethylpiperidin-4-yl)-N-methoxymethylurethane.

Phosphites and Phosphonates, Such as tris(nonylphenyl)phosphite, tris(2,4-di-tert-butylphenyl) phosphite, bis(2,4-di-tert-butylphenyl)pentaerythritol diphosphite, bis(2,6-di-tert-butyl-4-methylphenyl)pentaerythritol diphosphite, 2,2'-methylenebis(4,6-di-tert-butylphenyl)octyl phosphite, tetrakis(2,4-di-tert-butylphenyl)[1,1'-biphenyl]-4,4'-diylbisphosphonite, 2,2'-ethylidenebis(4,6-di-tert-butylphenyl)fluorophosphite, dioctadecyl pentaerythritol diphosphonite, 2-[[2,4,8,10-tetrakis(1,1-dimethyl-ethyl)dibenzo[d,f][1,3,2]dioxaphosphin-6-yl]oxy]-N,N-bis[2-[[2,4,8,10-tetrakis(1,1-dimethyl-ethyl)dibenzo[d,f][1,3,2]dioxaphosphin-6-yl]oxy]ethyl]ethanamine (CAS No. 80410-33-9), bis(2,4-di-tert-butyl-6-methylphenyl) ethyl phosphite, 2,4,6-tri-tert-butylphenyl 2-butyl-2-ethyl-1,3-propanediol phosphite, bis(2,4-dicumylphenyl)pentaerythritol diphosphite, Hydroxylamines, Such as amines, bis(hydrogenated tallow alkyl), oxidized, Secondary Arylamines, Such as N-(2-naphthyl)-N-phenylamine, 2,2,4-trimethyl-1,2-dihydroquinoline polymer (CAS No. 26780-96-11), N-2-propyl N'-phenyl-p-phenylenediamine, N-(1-naphthyl)-N-phenylamine, (benzenamine, N-phenyl-, reaction products with 2,4,4-trimethylpentene) (CAS No. 68411-46-1), 4-(1-methyl-1-phenylethyl)-N-[4-(1-methyl-1-phenylethyl)phenyl]aniline.

Lactones and Benzofuranones, Such as

Irganox HP 136 (CAS No. 181314.48-7)

Thioethers and Thioesters, Such as distearyl 3,3-thiodipropionate, dilauryl 3,3'-thiodipropionate, ditetradecyl thiodipropionate, di-n-octadecyl disulphide.

UV Absorbers, Such as (methanone, [methylenebis(hydroxymethoxyphenylene)] bis[phenyl-), (methanone, [1,6-hexane-diylbis[oxy(2-hydroxy-4,1-phenylene)]]bis(phenyl-), 2-benzoyl-5-methoxyphenol, 2,4-dihydroxybenzophenone, 2,2'-dihydroxy-1-methoxybenzophenone, 2-hydroxy-4-octyloxybenzophenone, 2-hydroxy-4-dodecyloxybenzophenone, 2-(2-hydroxy-4-hexyloxyphenyl)-4,6-diphenyl-1,3,5-triazine, 2,4-bis(2,4-dimethylphenyl)-6-(2-hydroxy-4-octyloxyphenyl)-1,3,5-triazine, 2-ethoxy-2'-ethyloxalic acid bisanilide, N-(5-tert-butyl-2-ethoxyphenyl)-N'-(2-ethylphenyl)oxamide, dimethyl(p-methoxybenzylidene)malonate, 2,2'-(1,4-phenylene)bis[3,1-benzoxazin-4-one], N'-(4-ethoxycarbonylphenyl)-N-methyl-N-phenylformamidine, 4-methoxycinnamic acid 2-ethylhexyl ester, 4-methoxycinnamic acid isoamyl ester, 2-phenylbenzimidazole-5-sulphonic acid, 2-cyano-3,3-diphenylacrylic acid 2-ethylhexyl ester, 2-ethylhexyl salicylate, 3-(4-methylbenzylidene)bornan-2-one, Chelators, Such as ethylenediaminetetraacetate (EDTA), ethylenediamine, acetylacetone, nitrotriacetic acid, ethylene glycol bis(β-aminoethyl ether)-N,N-tetraacetic acid, 2,2'-bipyridine, 4,4'-dimethyl-2,2'-bipyridine, 2,2',6',2''-terpyridine, 4,4'-diphenyl-2,2'-bipyridine, 2,2'-bipyridine-3,3-diol, 1,10-phenanthroline, 4-methyl-1,10-phenanthroline, 5-methyl-1,10-phenanthroline, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,4,7,9-tetramethyl-1,10-phenanthroline, N,N,N',N'-tetramethylethylenediamine, 2-hydroxyquinoline, 8-hydroxyquinoline, 2-hydroxy-4-methylquinaldine, 5-chloro-8-hydroxyquinoline, 5,7-dichloro-8-hydroxyquinoline, 2,4-quinolinediol, 2-quinolinethiol, 8-quinolinethiol, 8-aminoquinoline, 2,2'-biquinoline, 2-quinoxalinol, 3-methyl-2-quinoxalinol, 2,3-dihydroxyquinoxaline, 2-mercaptopyridine, 2-dimethylaminopyridine, 1,2-bis(dimethylphosphino)ethane, 1,2-bis(diphenylphosphino)ethane, 1,3-bis(diphenylphosphino)propane, 1,4-bis(diphenylphosphino)butane, polyaspartic acid, iminodisuccinate.

Iodine-containing compounds, more particularly biocides, are degraded in particular in the presence of the dryers described in more detail above. Although the strongest effects are observed in the presence of these dryers, a series of further paint components also have a destabilizing effect on iodine-containing compounds, more particularly biocides. These include organic and inorganic pigments, fillers, anti-skinning agents, rheological additives such as, for example, anti-settling agents and thixotropic agents, further compounds, particularly biocides such as fungicides, bactericides, anti-fouling agents and algicides, solvents, process additives, plasticizers, UV stabilizers and heat stabilizers, corrosion inhibitors, etc. The aziridine compounds also display a strongly stabilizing effect here.

The compositions of the invention, used in oxidatively drying binder preparations, and the binder preparations of the invention themselves exhibit a significant reduction in drying time as compared with unstabilized iodine-containing systems, particularly systems containing IPBC.

The invention also relates to a process for preparing the binder formulations by mixing of the individual components, preferably at a temperature of 5 to 30° C., more particularly of 15-25° C.

Preferred binder formulations are those obtainable by the preparation process of the invention.

The binder formulations of the invention are used preferably as coating materials, more particularly as paints, varnishes, primers, impregnating systems and stains. Accordingly, the invention also provides for the use of the binder formulations of the invention as coating materials.

The invention further provides for the use of the composition of the invention for protecting industrial materials against destruction or infestation by microorganisms.

The compositions of the invention are suitable for protecting industrial materials. Industrial materials in the present context are non-living materials which have been prepared for use in industry. The industrial materials are, for example, adhesives, sizes, paper and cardboard, textiles, leather, wood, wood-based materials, coating materials and plastics articles, cooling lubricants and other materials which may be infested or decomposed by microorganisms.

Examples of microorganisms which may bring about degradation or alteration of the industrial materials include bacteria, fungi, yeasts, algae and slime organisms. The active compounds of the invention act preferably against fungi, more particularly moulds, wood-discolouring and wood-destroying fungi (Basidiomycetes) and also against slime organisms and bacteria.

Microorganisms of the Following Genera May be Mentioned by Way of Example:

*Alternaria*, such as *Alternaria tenuis*,
*Aspergillus*, such as *Aspergillus niger*.
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*.
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

The invention further provides the industrial materials comprising at least one iodine-containing compound, more particularly biocide, and at least one aziridine compound.

EXAMPLES

In the examples below, stability tests accelerated by storage at elevated temperature are carried out. The IPBC was assayed in all cases by HPLC.

Examples 1-4

Examples 1-4 use investigations to illustrate the sensitivity of IPBC with regard to transition metal dryers.

Example 1

IPBC

IPBC (3.4900 g; 0.0124 mol) is weighed out into a 50 ml volumetric flask and made up to 50 ml with tripropylene glycol monomethyl ether (Dowanol® TPM), and the solution is transferred to an inertised ($N_2$) 100 ml two-necked flask. After a sample has been taken to determine the initial IPBC content at time ($t_0$), the flask is lowered into an oil bath set to a temperature of 60° C., and the solution is stirred under nitrogen. For determination of the IPBC content over time, a Hamilton syringe is used to take samples at intervals, which are cooled to room temperature and then subjected to defined dilution. For this purpose, 0.5 ml of the sample in the volumetric flask is made up to 10 ml with acetonitrile (MeCN) and subjected to direct measurement (HPLC). Table 1 shows the course of the IPBC fractions as a function of time.

TABLE 1

Determination of IPBC content (measurement error approx. 10%).

| Time [h] | Relative IPBC content [%] |
|---|---|
| 0 | 100 |
| 0.5 | 94 |
| 1 | 100 |
| 2 | 93 |
| 4 | 99 |
| 7 | 93 |

Example 2

IPBC+Co Dryer

IPBC (3.532 g; 12.60 mmol) is weighed out into a 50 ml volumetric flask and made up to 50 ml with tripropylene glycol monomethyl ether (Dowanol® TPM), and the solution is transferred to an inertised ($N_2$) 100 ml two-necked flask, which has been charged beforehand with 1.260 g of Octasoligen®-Cobalt 12 from Borchers (cobalt(II) carboxylates of branched $C_6$-$C_{19}$ fatty acids, in solution in white spirit, 12% Co content; 2.566 mmol of Co). After 1 minute of stirring and the taking of a sample for determination of the initial IPBC content at time ($t_0$), the flask is lowered into an oil bath set to a temperature of 60° C., and the solution is stirred under nitrogen. The IPBC content is determined as in Example 1. Table 2 shows the course of the IPBC content as a function of time.

TABLE 2

Determination of IPBC content (measurement error approx. 10%).

| Time [h] | Relative IPBC content [%] |
|---|---|
| 0 | 100 |
| 0.5 | 87 |
| 1 | 82 |
| 2 | 72 |
| 4 | 55 |
| 7 | 37 |

Example 3

IPBC+Aziridine Comp.+Co Dryer

IPBC (3.741 g; 13.31 mmol) is weighed out into a 50 ml volumetric flask and made up to 50 ml with tripropylene glycol monomethyl ether (Dowanol® TPM), and the solution is transferred to an inertised ($N_2$) 100 ml two-necked flask, which has been charged beforehand with 1.252 g of Octasoligen®-Cobalt 12 from Borchers (cobalt(II) carboxylates of branched $C_6$-$C_{19}$ fatty acids, in solution in white spirit, 12% Co content; 2.549 mmol of Co). Following addition of 7.551 g (16.64 mmol) of trimethylolpropane tris[3-(2-methyl-1-aziridinyl)propionate] (Crosslinker CX-100 from DSM), 1 minute of stirring and the taking of a sample for determination of the initial IPBC content at time ($t_0$), the flask is lowered into an oil bath set to a temperature of 60° C., and the solution is stirred under nitrogen. The IPBC content is determined as in Example 1. Table 3 shows the course of the relative IPBC content as a function of time.

TABLE 3

Determination of IPBC content

| Time [h] | Relative IPBC content [%] |
|---|---|
| 0 | 100 |
| 0.5 | 109 |
| 1 | 101 |
| 2 | 105 |
| 4 | 97 |
| 7.5 | 93 |

Within the bounds of measurement error (approx. 10%), no degradation of IPBC is found.

Example 4

IPBC+Aziridine Comp.+Co Dryer

IPBC (1.3583 g, 4.832 mmol) is weighed out into a 20 ml volumetric flask and made up to 20 ml with tripropylene glycol monomethyl ether (Dowanol® TPM), and the solution is transferred to an inertised ($N_2$) 50 ml two-necked flask, which has been charged beforehand with 0.5123 g of Octasoligen®-Cobalt 12 from Borchers (cobalt(II) carboxylates of branched $C_6$-$C_{19}$ fatty acids, in solution in white spirit, 12% Co content; 1.043 mmol of Co). Following addition of 5.018 g (19.97 mmol) of 7-tolylsulphonyl-7-azabicyclo[4.1.0]heptane, 1 minute of stirring and the taking of a sample for determination of the initial IPBC content at time ($t_0$), the flask is lowered into an oil bath set to a temperature of 60° C. and the solution is stirred under nitrogen. The IPBC content is determined as in Example 1. Table 4 shows the course of the relative IPBC content as a function of time.

TABLE 4

Determination of IPBC content

| Time [h] | Relative IPBC content [%] |
|---|---|
| 0 | 100 |
| 0.5 | 88 |
| 1 | 86 |
| 2 | 80 |
| 4 | 64 |
| 7 | 58 |

Within the bounds of measurement error (approx. 10%), a level of IPBC degradation significantly lower by comparison with Example 2 is found.

Example 5

This example demonstrates the stabilizing effect of the aziridine trimethylolpropane tris[3-(2-methyl-1-aziridinyl)propionate](Crosslinker CX-100 from DSM) and also of the aziridine trimethylolpropane tris[3-(1-aziridinyl)propionate] (Corial Härter AN from BASF) on the IPBC in the presence of a transition metal dryer (Co) and of a metal oxide pigment (iron oxide) in a typical, alkyd-based coating system (alkyd stain A). The coating system was equipped using compositions as per Table 5:

TABLE 5

| Concentrate I | | Concentrate II | |
|---|---|---|---|
| IPBC | 30% by weight | IPBC | 30% by weight |
| Rhodiasolv DIB* | 70% by weight | Crosslinker CX-100** | 15% by weight |
| | | Rhodiasolv DIB* | 55% by weight |

| Concentrate III | |
|---|---|
| IPBC | 30% by weight |
| Corial Harter AN*** | 10% by weight |
| Rhodiasolv DIB* | 60% by weight |

*Mixture of diisobutyl adipate, diisobutyl glutarate and diisobotyl succinate, from Rhodia.
**Trimethylolpropane tris[3-(2-methyl-1-aziridinyl)propionate]
***Trimethylolpropane tris[3-(1-aziridinyl)propionate]

The formula of the alkyd stain used is shown in Table 6 (alkyd stain A).

The stabilization is determined by implementation of an accelerated ageing test. For this purpose the additised paint system is charged to tightly sealing 200 ml glass bottles, with only a minimum amount of air remaining in the container, and subjected to storage at 40° C. The results can be seen from Table 7.

TABLE 6

Formula of a pigmented alkyd-based stain.

| Ingredients | Ingredients of alkyd stain A-I [%] | Ingredients of alkyd stain A-II [%] |
|---|---|---|
| Alkyd stain A Vialkyd VAF 4349, 80 SD 60, from Cytec | 22.5 | 22.5 |
| Polar solvent Texanol, from Eastman | 5.0 | 5.0 |
| Rheology additive BYK E411, from BYK | 0.4 | 0.4 |
| Shellsol D60, from Shell Chemicals | 65.47 | 65.47 |
| MK-Solcolor red iron oxide 130M (pigment preparation), from MK Chemicals | 4.0 | 4.0 |
| Octa-Soligen ® 69 (contains 6% Co), from Borchers | 0.3 | 0.3 |
| Concentrate I | 2.33 | — |
| Concentrate II | — | 2.33 |

Alkyd stain A-III = 97.67% alkyd stain A + 2.33% concentrate III.

TABLE 7

Stability of IPEC in alkyd stains A-I and A-II at 40° C.

| Stain | IPBC [%], initial | IPBC [%], 2 weeks | IPBC [%], 4 weeks |
|---|---|---|---|
| A-I (aziridine-free) | 0.71 | 0.11 | 0 |
| A-II (containing aziridine) | 0.69 | 0.67 | 0.62 |
| A-III (containing aziridine) | 0.67 | 0.67 | 0.63 |

Example 6

This example demonstrates the stabilizing effect of the aziridine trimethylolpropane tris[3-(2-methyl-1-aziridinyl) propionate] (Crosslinker CX-100 from DSM) on the IPBC in a commercial high-build woodstain "alkyd stain B" (containing alkyd resin, white spirit, iron oxide pigment, dryer, butanone oxime, UV absorbers and additives) in comparison to epoxides of the kind described, for example, in EP 1115287 B1. The coating system is equipped using compositions as per Table 8:

TABLE 8

| Concentrate I | | Concentrate II | |
|---|---|---|---|
| IPBC | 30% by weight | IPBC | 30% by weight |
| Rhodiasolv DIB* | 70% by weight | Crosslinker CX-100** | 15% by weight |
| | | Rhodiasolv DIB* | 55% by weight |

| Concentrate III | | Concentrate IV | |
|---|---|---|---|
| IPBC | 30% by weight | IPBC | 30% by weight |
| DTGE[1] | 30% by weight | EEC[2] | 15% by weight |
| Rhodiasolv DIB* | 40% by weight | Rhodiasolv DIB* | 55% by weight |

For definition of * and ** see Table 5;
[1] Mixture containing the epoxides 2-[(dodecyloxy)methyl]oxirane and 2-[(tetradecyloxy)methyl]oxirane (CAS No. 68609-97-2), e.g. from Aldrich.
[2] (3,4-epoxycyclohexyl)methyl-3,4-epoxycyclohexylcarboxylate (CAS No. 2386-87-0), e.g. from Aldrich.

In addition, a commercially available IPBC formulation (Troy Polyphase® 920, containing 20% IPBC) was used which is referred to below as concentrate V. The high-build woodstains under investigation, equipped with 0.7% by weight of IPBC (alkyd stain B-I to alkyd stain B-V), were prepared by mixing 97.67% of the aforementioned alkyd stain B with 2.33% by weight of each of concentrates I to V, respectively.

The stabilization is determined by implementation of an accelerated ageing test. For this purpose, the additised paint system was charged to tightly sealing 200 ml glass bottles, with only a minimum amount of air remaining in the container, and subjected to storage at 40° C. The results are apparent from Table 9, according to which only the alkyd stain B-II equipped with the aziridine "Crosslinker CX-100" shows no significant IPBC degradation after 4 weeks of storage at 40° C.

TABLE 9

Stability of IPBC in alkyd stains B-I to B-V at 40° C.

| Alkyd stain B | Residual IPBC content [%] relative to initial level | | | | | |
|---|---|---|---|---|---|---|
| | Initial | 2 weeks | 4 weeks | 8 weeks | 12 weeks | 16 weeks |
| -I | 100 | 24 | 0 | — | — | — |
| -II | 100 | 95 | 95 | 86 | 56 | 7 |
| -III | 100 | 9 | 0 | — | — | — |
| -IV | 100 | 30 | 3 | 0 | — | — |
| -V | 100 | 52 | 0 | — | — | — |

Example 7

This example shows that the addition of the aziridine trimethylolpropane tris[3-(2-methyl-1-aziridinyl)propionate](Crosslinker CX-100 from DSM) to the commercial high-build woodstain "alkyd stain B" (see Example 6) is able to prevent the unwanted prolongation of the drying time of the coating material that is caused by its additisation with IPBC. The stains investigated are set out in Table 10.

TABLE 10

| Constituent | Alkyd stain B Fraction [%] | Alkyd stain B-VI Fraction [%] | Alkyd stain B-VII Fraction [%] |
|---|---|---|---|
| Alkyd stain B | 100.0 | 99.50 | 99.20 |
| IPBC (e.g. Preventol ® MP 100) | — | 0.50 | 0.50 |
| Crosslinker CX-100* | — | — | 0.30 |

For definition of * see Table 5.

The drying times were determined with the freshly prepared stains and with the stains stored at 40° C. for 2 weeks (accelerated ageing test). For drying time determination, a film applicator was used to apply a 90 μm film of the respective stain to glass, and the drying times were determined using a drying time measuring instrument (e.g. BYK-Gardner), with measurements of the times required for initial drying and for through-drying of the film. The results of these investigations are set out in Table 11.

TABLE 11

Determination of drying times.

| | Fresh sample | | 2 weeks of storage at 40° C. | |
|---|---|---|---|---|
| | Initial drying [h] | Through-drying [h] | Initial drying [h] | Through-drying [h] |
| Alkyd stain B | 3.2 | 3.7 | 3.7 | 4.3 |
| Alkyd stain B-VI | 3.3 | 3.8 | 10.6 | >12 |
| Alkyd stain B-VII | 3.2 | 3.4 | 4.4 | 4.6 |

What is claimed is:

1. A binder formulation comprising:
   at least one alkyd resin binder,
   at least one iodine containing compound, and
   at least one aziridine compound of the formula (I)

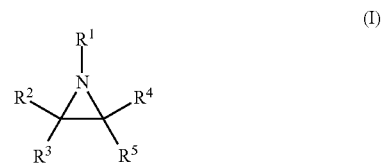

where
   $R^1$ is hydrogen, alkyl or cycloalkyl, each of which are unsubstituted or substituted and/or mono- or polyethylenically unsaturated, or in each case substituted or unsubstituted fullerenyl, aryl, alkoxy, alkoxycarbonyl, arylcarbonyl or alkanoyl,
   $R^2$, $R^3$, $R^4$ and $R^5$ independently of one another have the same definition as $R^1$ and additionally independently are halogen, hydroxyl, carboxyl, alkylsulphonyl, arylsulphonyl, nitrile, isonitrile, and/or $R^2$ and $R^4$, or $R^3$ and $R^5$, together with the carbon atoms to which they are attached, form a 5- to 10-membered carbocyclic ring which is unsubstituted or substituted and/or mono- or polyethylenically unsaturated.

2. The binder formulation according to claim 1, further comprising at least one transition metal dryer.

3. The binder formulation according w claim 1, further comprising at least one polar organic solvent.

4. The binder formulation according to claim 1, comprising
   1% to 80% by weight of the alkyd resin binder(s),
   0% w 50% by weight of colour pigments,
   0.01% to 5% by weight of the iodine-containing compound,
   0.001% to 5% by weight of the aziridine compound,
   2% to 97% by weight of solvent(s), and
   0.001% to 3% by weight of a transition metal dryer.

5. Industrial materials comprising the binder formulation according to claim 1.

6. The binder formulation according to claim 1, wherein the iodine-containing compound is selected from the group consisting of diiodomethyl p-tolyl sulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methylpropyl)-5-[(6-iodo-3-pyridinyl)methoxy-3(2H)-pyridazinone (CAS RN: 120955-77-3), iodofenfos, 3-iodo-2-propynyl 2,4,5-trichlorophenyl ether, 3-iodo-2-propynyl 4-chlorophenyl formal (IPCF), N-iodopropargyloxycarbonylalanine, N-iodopropargyloxycarbonylalanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-do-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

7. The binder formulation according to claim 1, wherein the iodine-containing compound is selected from the group consisting of 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-Iodo-2-propynyl thioxothioethylcarbamate, 3-iodo-2-propynyl carbamate (IPC), 3-bromo-23-diiodo-2-propenyl ethylcarbamate, 3-iodo-2-propynyl n-hexylcarbamate and 3-iodo-2-propynyl cyclohexylcarbamate.

8. The binder formulation according to claim 1, wherein the iodine-containing compound is selected from the group consisting of N-alkyl-iodotetrazoles, N-aryl-iodotetrazoles, and N-aralkyl-iodotetrazoles.

9. A binder formulation comprising:
    at least one alkyd resin binder,
    at least one iodine containing compound, and
    at least one aziridine compound of the formula (II)

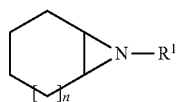

(II)

where
    the carbocyclic ring is unsubstituted or substituted by one or more substituents selected from the group consisting of halogen, hydroxyl, oxo, carboxyl, alkylsulphonyl, arylsulphonyl, nitrile, isonitrile, alkyl or cycloalkyl, each of which is unsubstituted or substituted and/or mono- or polyethylenically unsaturated, or substituted or unsubstituted fullerenyl, aryl, alkoxy, alkoxycarbonyl or alkanoyl, and
    n is a number from 0 to 6.

10. The binder formulation according to claim 9, further comprising at least one transition metal dryer.

11. The binder formulation according w claim 9, further comprising at least one polar organic solvent.

12. The binder formulation according to claim 9, comprising
    1% to 80% by weight of the alkyd resin binder(s),
    0% w 50% by weight of colour pigments,
    0.01% to 5% by weight of the iodine-containing compound,
    0.001% to 5% by weight of the aziridine compound,
    2% to 97% by weight of solvent(s), and
    0.001% to 3% by weight of a transition metal dryer.

13. Industrial materials comprising the binder formulation according to claim 9.

14. The binder formulation according to claim 9, wherein the iodine-containing compound is selected from the group consisting of diiodomethyl p-tolyl sulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methylpropyl)-5-[(6-iodo-3-pyridinyl)methoxy]-3(2H)-pyridazinone (CAS RN: 120955-77-3), iodofenfos, 3-iodo-2-propynyl 2,4,5-trichlorophenyl ether, 3-iodo-2-propynyl 4-chlorophenyl formal (IPCF), N-iodopropargyloxycarbonylalanine, N-iodopropargyloxycarbonylalanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

15. The binder formulation according to claim 9, wherein the iodine-containing compound is selected from the group consisting of 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

16. The binder formulation according to claim 9, wherein the iodine-containing compound is selected from the group consisting of N-alkyl-iodotetrazoles, N-aryl-iodotetrazoles, and N-aralkyl-iodotetrazoles.

* * * * *